United States Patent [19]
Vogt et al.

[11] Patent Number: 6,149,638
[45] Date of Patent: *Nov. 21, 2000

[54] EXTENSIBLE ABSORBENT ARTICLE INCLUDING FOLDED LAYERS ADJACENT THE ABSORBENT CORE

[75] Inventors: Robert Eugene Vogt; Timothy James Blenke, both of Neenah, Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 09/002,101

[22] Filed: Dec. 31, 1997

[51] Int. Cl.[7] .............................. A61F 13/15; A61F 13/20
[52] U.S. Cl. ............... 604/385.01; 604/378; 604/385.22
[58] Field of Search ..................... 604/358, 378, 604/385.1, 385.2, 385.01, 385.22

[56] References Cited

U.S. PATENT DOCUMENTS

| | | |
|---|---|---|
| H1511 | 12/1995 | Chappell et al. ............... 604/385.1 |
| H1558 | 7/1996 | Goulait et al. ............... 156/210 |
| 2,866,459 | 12/1958 | Sobelson . |
| 3,481,337 | 12/1969 | Rufto ................... 604/385.1 |
| 4,051,854 | 10/1977 | Aaron . |
| 4,474,846 | 10/1984 | Boland et al. . |
| 4,655,760 | 4/1987 | Morman et al. ............... 604/385 A |
| 4,657,802 | 4/1987 | Morman ................... 428/152 |
| 4,699,620 | 10/1987 | Bernardin ............... 604/385 A |
| 4,701,170 | 10/1987 | Wilson et al. ............... 604/385 A |
| 4,701,171 | 10/1987 | Boland et al. . |
| 4,701,172 | 10/1987 | Stevens . |
| 4,701,173 | 10/1987 | Zehner et al. . |
| 4,701,174 | 10/1987 | Johnson . |
| 4,701,176 | 10/1987 | Wilson et al. . |
| 4,704,114 | 11/1987 | Wilson et al. . |
| 4,704,116 | 11/1987 | Enloe . |
| 4,710,187 | 12/1987 | Boland et al. ............... 604/385.2 |
| 4,756,709 | 7/1988 | Stevens . |
| 4,770,656 | 9/1988 | Proxmire et al. ............... 604/393 |
| 4,808,176 | 2/1989 | Kielpikowski ............... 604/385.2 |
| 4,834,736 | 5/1989 | Boland et al. ............... 604/385.2 |
| 4,834,738 | 5/1989 | Kielpikowski et al. ............... 604/385.2 |
| 4,834,742 | 5/1989 | Wilson et al. ............... 604/389 |
| 4,838,885 | 6/1989 | Bernardin ............... 604/385.1 |
| 4,842,596 | 6/1989 | Kielpikowski et al. ............... 604/385.2 |
| 4,846,825 | 7/1989 | Enloe et al. ............... 604/385.1 |
| 4,847,134 | 7/1989 | Fahrenkrug et al. ............... 428/138 |
| 4,850,990 | 7/1989 | Huntoon et al. ............... 604/385.2 |
| 4,872,871 | 10/1989 | Proxmire et al. ............... 604/394 |
| 4,895,569 | 1/1990 | Wilson et al. ............... 604/386 |
| 4,936,840 | 6/1990 | Proxmire ............... 604/385.2 |
| 5,019,066 | 5/1991 | Freeland et al. ............... 604/385.2 |
| 5,226,992 | 7/1993 | Morman . |
| 5,246,433 | 9/1993 | Hasse et al. ............... 604/396 |
| 5,356,403 | 10/1994 | Faulks et al. ............... 604/385.1 |
| 5,376,198 | 12/1994 | Fahrenkrug et al. ............... 156/164 |
| 5,393,599 | 2/1995 | Quantrille et al. ............... 428/284 |
| 5,440,764 | 8/1995 | Matsushita ............... 2/401 |

(List continued on next page.)

FOREIGN PATENT DOCUMENTS

| | | |
|---|---|---|
| 1316651 | 4/1993 | Canada . |
| WO 97/43994 | 11/1997 | WIPO . |

*Primary Examiner*—Mark O. Polutta
*Attorney, Agent, or Firm*—Thomas D. Wilhelm

[57] ABSTRACT

An absorbent article includes an absorbent pad and an extensible outer cover. The absorbent pad comprises an absorbent core surrounded by a first folded layer and optionally a second folded barrier layer. Folds of the first and second folded layers unfold and thereby open when an extensible bodyside liner and/or outer cover of the absorbent article are extended. The folds, when opened, extend the respective folded layers in a respective cross-direction or longitudinal direction. Extension of the folds of the first and second folded layers prevents tearing of the absorbent pad and damage to, or release of superabsorbent material from the absorbent pad during extension of the absorbent article. The folds can comprise T-folds, C-folds, pleated arrangements, corrugations, or the like.

36 Claims, 4 Drawing Sheets

U.S. PATENT DOCUMENTS

| | | | |
|---|---|---|---|
| 5,464,401 | 11/1995 | Hasse et al. | 604/385.1 |
| 5,470,639 | 11/1995 | Gessner et al. | 428/152 |
| 5,496,429 | 3/1996 | Hasse et al. | 156/73.3 |
| 5,518,801 | 5/1996 | Chappell et al. | 428/152 |
| 5,531,732 | 7/1996 | Wood | 604/391 |
| 5,543,206 | 8/1996 | Austin et al. | 428/198 |
| 5,591,148 | 1/1997 | McFall et al. | 604/385.1 |
| 5,762,641 | 6/1998 | Bewick-Sonntag et al. | 604/378 |
| 5,954,705 | 9/1999 | Sawaki et al. | |

EXTENSIBLE ABSORBENT ARTICLE INCLUDING FOLDED LAYERS ADJACENT THE ABSORBENT CORE

FIELD OF THE INVENTION

Absorbent articles such as infant diapers, training pants, adult incontinence products, and the like are well known. Such absorbent articles have achieved wide acceptance due to their ability to receive and absorb body exudates, whether large amounts or small, and generally include an absorbent core therein.

In typical absorbent articles, an absorbent pad has an absorbent core contained within first and second tissues. The absorbent pad is located between an outer cover and a bodyside liner.

This invention pertains to improvements in extensible absorbent articles for use in receiving and absorbing body exudates. The outer cover generally comprises a material extensible in at least one direction. An adhesive is generally applied to a first inner surface of the outer cover. First and second layers, disposed on opposing sides of the absorbent core are secured to each other outwardly of the absorbent core. Both of the first and second layers comprise improved structures whereby the first and second layers can in cooperation with extension of the outer cover unfold or open so that the absorbent pad does not tear, and accordingly does not release absorbent materials when the absorbent article is extended.

BACKGROUND OF THE INVENTION

In general, absorbent articles should comfortably fit the body of a wearer. Conventional absorbent articles include an absorbent pad having an absorbent core contained in a wrap comprising a first outer cover tissue and/or a second bodyside liner tissue.

However, in conventional structures, the outer cover is typically adhesively secured to the tissue of the absorbent pad. In such embodiments, extending the outer cover in the cross-direction extends the absorbent pad in the cross-direction. In such embodiments, the force used to extend the outer cover, and thence the absorbent pad, can tear or otherwise damage the tissue of the absorbent pad. Since the absorbent pad is typically a sealed enclosure, namely an absorbent core enclosed within the combination of an outer cover tissue and a bodyside liner tissue, tearing the absorbent pad, namely either the outer cover tissue or the bodyside liner tissue, can release superabsorbent particles and other absorbent core materials into contact with the body of the wearer. Such materials can irritate the skin of the wearer, and such release indicates failure of the absorbent article to perform properly. Therefore, it is highly desirable to find a way to prevent tearing or other structural failure of the absorbent pad in absorbent articles which use an extensible outer cover and an extensible bodyside liner.

SUMMARY OF THE DISCLOSURE

In the present invention, an absorbent article includes an absorbent core having an outer perimeter, a folded layer of material including at least one fold therein and having a first surface disposed adjacent a first side of the absorbent core, an extensible outer cover having a surface disposed in surface-to-surface relationship with a second surface of the folded layer, and a pattern of adhesive disposed at least in part between the folded layer and the outer cover, the pattern of adhesive mounting the folded layer to the outer cover such that, in response to extension of the outer cover, the folded layer can extend with the outer cover by opening of the fold, the folded layer not tearing or otherwise releasing superabsorbent material from the absorbent core.

In some embodiments, the at least one fold comprises a first pleat, the folded layer including a second pleat spaced widthwise of the absorbent article from the first pleat. A first line of adhesive can be disposed between the pleats such that extension of the outer cover causes extension of the folded layer at both pleats.

In many embodiments, the folded layer comprises a substantially non-extensible tissue material.

In some embodiments, the fold of the folded layer comprises a corrugation. The folded layer can include a multiplicity of corrugations providing for extension of the folded layer in the cross-direction. Substantially the entire surface can be encompassed in a pattern of the corrugations.

In some embodiments, folds of the folded layer comprise T-folds and in other embodiments, the folds comprise C-folds.

In some embodiments, the pattern of adhesive includes at least one line of adhesive extending along the length of the absorbent article, and securing the outer cover to the folded layer at an unfolded portion of the folded layer.

In some embodiments, a second line of adhesive, disposed between the outer cover and the folded layer, extends the length of the absorbent article and secures the outer cover to the folded layer at a second unfolded portion of the folded layer. The first and second lines of adhesive can extend effectively along the entire length of the absorbent article and thereby assist in sealing ends of the bodyside liner and the outer cover at front and rear edges of the absorbent article.

In many embodiments, the absorbent article includes a bodyside liner having a body contacting surface and an opposing surface mounted in surface-to-surface relationship to at least a portion of the outer cover.

In some embodiments, the absorbent article includes a second folded barrier layer of material disposed between the second side of the absorbent core and the bodyside liner.

In some embodiments, the second folded barrier layer is adhesively secured to the first folded layer outwardly of the perimeter of the absorbent core.

In some embodiments, the first folded layer and the second folded barrier layer both comprise non-extensible tissues.

In some embodiments, the bodyside liner is extensible in at least the cross-direction.

In some embodiments, the bodyside liner, the outer cover, and the first and second folded layers are all extendible in the cross-direction during placement of the absorbent article on a wearer, the extension of the folded layers at the folds preventing tearing of either of the first folded layer and the second folded barrier layer during extension of the absorbent article, and thus avoiding release of superabsorbent material from the absorbent pad.

In another embodiment, the absorbent article comprises an extensible outer cover, a bodyside liner mounted in surface-to-surface relationship to at least a portion of a first inner surface of the outer cover, an absorbent pad disposed between the bodyside liner and the outer cover, the absorbent pad comprising an absorbent core having an outer perimeter, a first side, and an opposing second side, the absorbent pad including a first folded layer of material disposed between the first side of the absorbent core and the outer cover, and a second folded barrier layer of material disposed between the second side of the absorbent core and the bodyside liner, and a pattern of adhesive disposed between one of (i) the outer cover and the first folded layer and (ii) the bodyside liner and the second folded layer, accommodating extension of the respective one of the folded layers in combination with extension of the corresponding adhered one of the outer cover and the bodyside liner.

In some embodiments, the pattern of adhesive is disposed between the bodyside liner and the second folded layer such that extension of the outer cover and the bodyside liner can extend the first folded layer and the second folded layer within the absorbent article.

In some embodiments, the pattern of adhesive includes an array of adhesive extending in the longitudinal direction on opposing sides of a surface of the bodyside liner, outwardly from a perimeter of the absorbent pad.

In some embodiments the pattern of adhesive includes an array of adhesive extending in the longitudinal direction on opposing sides of the first inner surface of the outer cover, outwardly from a perimeter of the absorbent pad.

In some embodiments, a line of adhesive extending in the longitudinal direction between the outer cover and the first folded layer assists in maintaining alignment of the absorbent pad in the absorbent article.

In some embodiments, the bodyside liner and the outer cover are extensible in at least the cross-direction, and the first folded layer and the second folded barrier layer each have at least one fold extending along substantially the entire length of the absorbent article in the longitudinal direction.

In some embodiments, the bodyside liner, the outer cover, and the first and second folded layers all extend in the cross-direction during placement of the absorbent article on a wearer, the extension of the folded layers being enabled by the unfolding of respective folds of the first layer and the second layer.

In some embodiments, the pattern of adhesive comprises laterally spaced arrays of swirls of adhesive disposed along the length of the outer cover outwardly from the absorbent core.

In another embodiment of the invention, an absorbent pad for use in an absorbent article comprises an absorbent core having an outer perimeter, a first folded layer of material having at least one fold disposed at a first side of the absorbent core, and a second folded barrier layer of material having at least one fold and being disposed at a second side of the absorbent core, the first folded layer and the second folded layer extending beyond the perimeter of the absorbent core, and an adhesive securing the first folded layer to the second folded barrier layer outwardly of the perimeter of the absorbent core.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in absorbent articles, but it should be understood that potential uses of the structures of the present invention need not be limited to the context of absorbent articles.

As used herein and in the claims that follow, the phrase "absorbent article" is meant to include diapers, training pants, adult incontinence articles, feminine hygiene products, and the like. Such articles generally receive and/or store urine and/or fecal material, or have a significant other absorbent function.

As used herein and in the claims that follow, the term "folds" includes T-folds, C-folds, pleated arrangements, corrugations, or other physically arranged elements that are able to extend outwardly, by virtue of change of structural form or arrangement, rather than extension of elastic materials, with respect to their original relaxed configurations.

Figure 1:
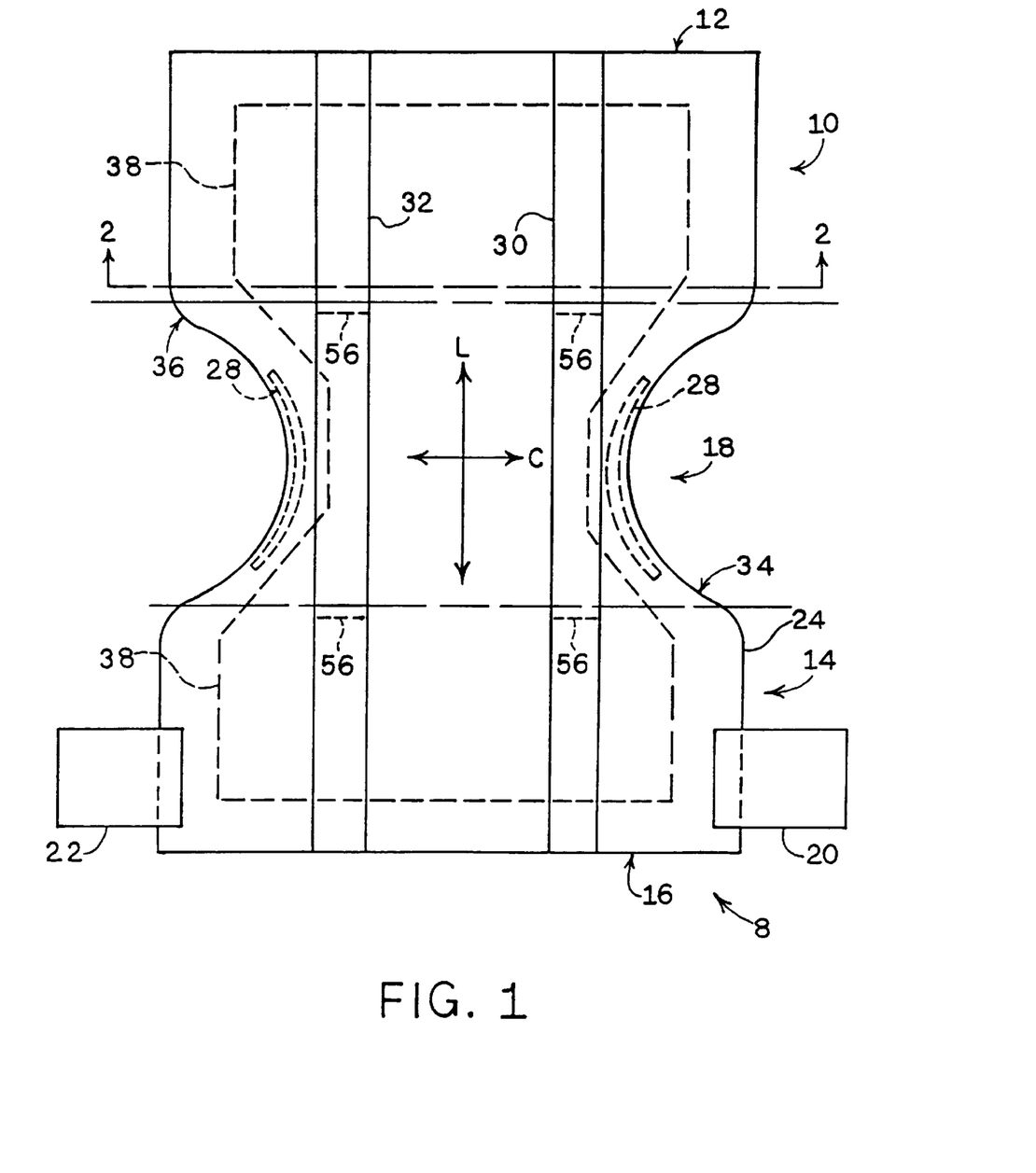
FIG. 1 shows a top view of a first embodiment of absorbent articles of the invention.

FIG. 1 is a representative plan view of an absorbent article 8 of one embodiment of the present invention, in its uncontracted state (i.e. with all elastic-induced gathering and contraction removed). Absorbent article 8, shown in FIG. 1, includes a front portion 10 having a front edge 12, a rear portion 14 having a rear edge 16, and a crotch portion 18 between front portion 10 and rear portion 14. Fastening tabs 20, 22 are secured to and extend outwardly from opposing sides of bodyside liner 24 in rear portion 14. Extensible outer cover 26 (shown in FIG. 2) lies in surface-to-surface relationship with bodyside liner 24. Leg elastics 28 provide generally longitudinal retractable extensibility and support in crotch portion 18. Containment flaps 30, 32 extend longitudinally along the length of absorbent article 8 inwardly of respective side edges 34, 36 of the absorbent article. Containment flaps 30, 32 are typically secured to bodyside liner 24. Absorbent pad 38 (shown in FIG. 2) may have an hour-glass shape and is disposed between bodyside liner 24 and outer cover 26.

Figure 2:
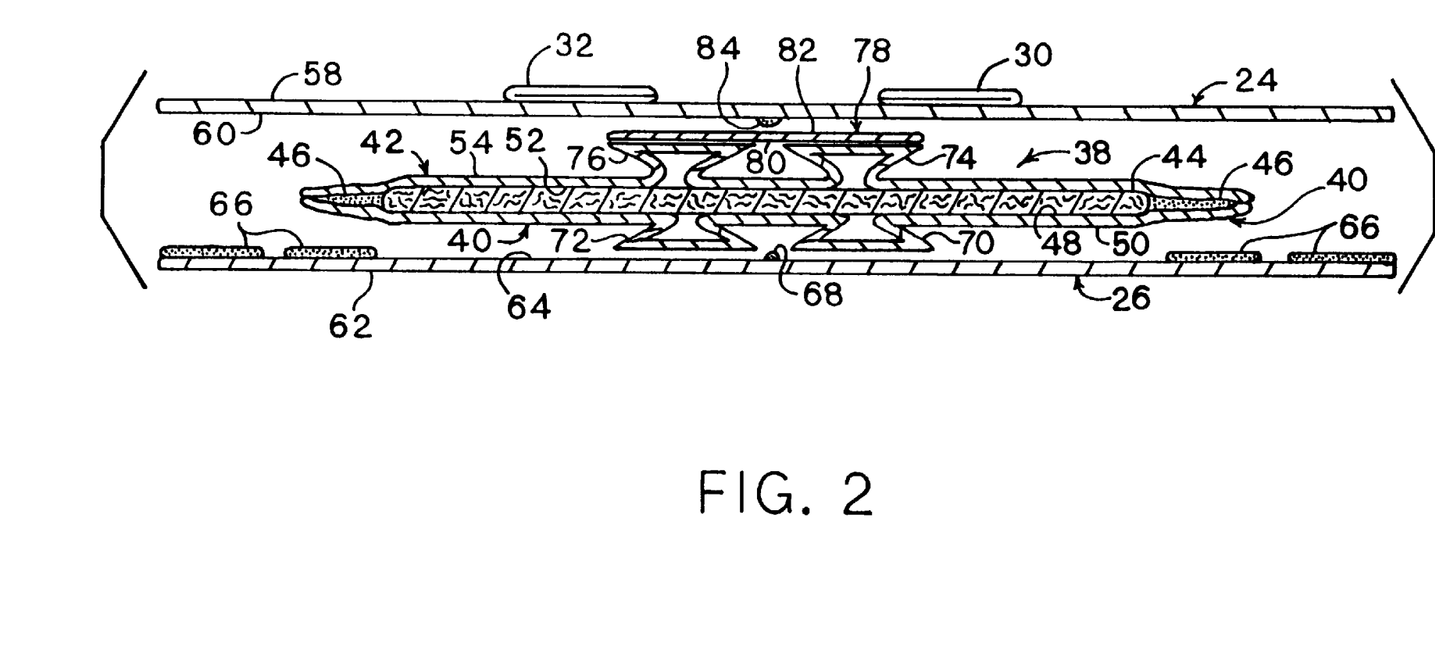
FIG. 2 shows a cross section of the absorbent article taken at line 2—2 of FIG. 1.

FIG. 2 illustrates a cross-section view taken at 2—2 of FIG. 1. Bodyside liner 24 and outer cover 26 are spaced away from each other for purposes of illustration. In a finished product, bodyside liner 24 and outer cover 26 are secured to each other by adhesive 66.

Absorbent pad 38 is located between bodyside liner 24 and outer cover 26. Absorbent pad 38 includes a first folded layer 40 and a second folded barrier layer 42, in combination surrounding an absorbent core 44. An adhesive 46 secures first folded layer 40 and second folded barrier layer 42 to each other. Thus first folded layer 40 and second folded barrier layer 42 envelope absorbent core 44 and thereby form absorbent pad 38. First folded layer 40 includes a first inner surface 48 and a second opposing outer surface 50. Likewise, second folded barrier layer 42 includes a first inner surface 52 and a second opposing outer surface 54. Absorbent pad 38 receives and retains exudates that pass through bodyside liner 24. Adhesive 46 secures a portion of first surface 48 of first folded layer 40 to first surface 52 of second folded barrier layer 42 about an outer perimeter of absorbent core 44.

Bodyside liner 24 has a first body facing surface 58 and a second opposing surface 60. Outer cover 26 includes a first outer surface 62 and a second opposing inner surface 64. A layer of adhesive 66 is disposed on second inner surface 64 of outer cover 26 and secures the outer cover to second surface 60 of bodyside liner 24.

In the preferred embodiments of the invention, outer cover 26 and bodyside liner 24 are extensible elements. Preferably at least one of the elements is resiliently extensible. Outer cover 26 preferably is extensible at least in cross-direction "C". In such an arrangement, extension of outer cover 26, if firmly secured to absorbent pad 38 at the entirety of first folded layer 40, as in the prior art, applies force to the absorbent pad. Such force may cause first folded layer 40 and/or second folded barrier layer 42 to tear and thus allow superabsorbent material to escape from absorbent pad 38. Such release of superabsorbent can cause discomfort to a wearer and is considered product failure.

Therefore, in the invention, a line of adhesive 68 is disposed in longitudinal direction "L" at approximately the center of second surface 64 of outer cover 26 so that the adhesive secures the outer cover to first folded layer 40 between first and second T-folds 70, 72 of the first folded layer.

Line of adhesive 68 secures outer cover 26 to first folded layer 40 along the longitudinal direction thus enabling extension of the outer cover in cross-direction "C". T-folds 70, 72 of first folded layer 40 are not contacted or affected by any adhesive. Therefore, when outer cover 26 of absorbent article 8 is extended in cross-direction "C", T-folds 70, 72 open and extend outwardly with the outer cover. Therefore, no significant loading is applied to absorbent pad 38, and no tearing of layer 40, potentially releasing absorbent material from the pad, occurs. Line of adhesive 68 also assists in maintaining alignment of absorbent pad 38 in absorbent article 8 by impeding angular movement of the pad with respect to outer cover 26.

FIG. 2 also illustrates the arrangement of second folded layer 42. Second folded layer 42 includes first and second T-folds 74, 76. There preferably is no securement between second folded layer 42 and bodyside liner 24. However, a line of adhesive (not shown) similar to line of adhesive 68 can extend along the center in the longitudinal direction, between surge layer 78 and absorbent pad 38, so long as the line of adhesive does not contact T-folds 74, 76. In operation, second folded layer 42 operates in a similar manner to, and in combination with, first folded layer 40. Thus, as extensible outer cover 24 and bodyside liner 26 extend in cross-direction "C". T-folds 74, 76 unfold and open. T-folds 70, 72 of first folded layer 40 also unfold and open. Opening of T-folds 70, 72, 74, 76 prevents development of significant stress on first and second folded layers 40, 42, which stress could tear either or both of layers 40, 42 open and thereby release absorbent material from absorbent pad 38.

FIG. 2 also illustrates surge layer 78 having a first surface 80 and a second surface 82. First surge layer surface 80 is disposed in surface-to-surface relationship with second surface 54 of second folded layer 42. Since no adhesive is directly applied between bodyside liner 24 and absorbent pad 38, the bodyside liner has relatively free mobility with respect to the absorbent pad.

A line of adhesive 84 disposed in the longitudinal direction "L" extends along the center of bodyside liner 24. Adhesive 84 thus secures bodyside liner 24 to second surface 82 of surge layer 78 along a longitudinal centerline, thereby securing surge layer 78 at a proper location to bodyside liner 24 for use in absorbent article 8. Having a longitudinal line of adhesive 84 allows bodyside liner 24 freedom to extend outwardly in the cross-direction "C" without significant resistance from surge layer 78 whereby the integrity of the surge layer is typically not threatened by such extension. Thus surge layer 78 is relatively free to move with respect to absorbent pad 38.

Adhesive 84 preferably comprises a hot melt adhesive extending in longitudinal direction "L" along the center of surge layer 78, as illustrated in FIG. 2.

Fastening tabs 20, 22 can comprise hooks of a hook and loop fastener system for securing rear portion 14 of absorbent article 8 to front portion 10. Other well known securing elements can be used to support absorbent article 8 on the user. For example, a cohesive system, an adhesive fastener system, or the like, may be utilized as securing elements, with suitable cooperating elements on front portion 10, as necessary, to support absorbent article 8 on the wearer. One example of a fastening tab is shown in U.S. patent application Ser. No. 421,640 filed Apr. 13, 1995 by Zehner et al, titled "Multi-Attachment Fastening System" the disclosure of which is hereby incorporated by reference in its entirety, to the extent such disclosure is consistent (not contradictory) with the subject matter disclosed herein.

Fastening tabs 20, 22 can be permanently secured to rear portion 14 of absorbent article 8 by, for example, ultrasonic bonding, adhesives, stitching, or other conventional and known methods of securement.

Figure 3:
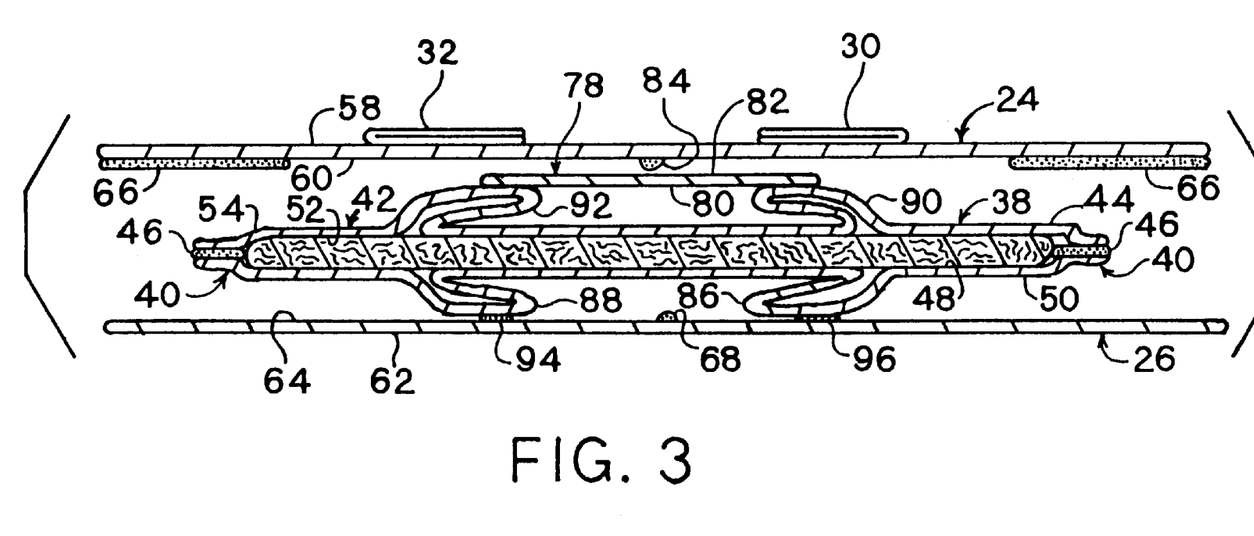
FIG. 3 shows a cross section of a second embodiment of absorbent articles of the invention having first and second layers including C-folds.

As representatively shown in FIGS. 1 and 3, bodyside liner 24 and outer cover 26 generally are coextensive and have length and width dimensions larger than the dimensions of absorbent pad 38. Thus bodyside liner 24 is generally superimposed over the entirety of the surface of outer cover 26, thereby defining the periphery of absorbent article 8. Absorbent pad 38 is disposed between outer cover 26 and bodyside liner 24 inboard of the periphery of absorbent article 8.

Bodyside liner 24 includes first skin-facing surface 58 which is compliant, soft-feeling, and non-irritating to the wearer's skin. Further, bodyside liner 24 must be sufficiently porous to be permeable to aqueous liquids, enabling such liquid to penetrate and pass through its thickness.

A suitable bodyside liner 24 may be manufactured from a wide selection of web materials, such as porous foams, reticulated foams, apertured plastic films, woven and/or nonwoven natural fibers, synthetic fibers, or a combination of natural and synthetic fibers. Bodyside liner 24 is typically employed to help isolate the wearer's skin from liquids held in absorbent pad 38. Various woven and nonwoven fabrics can be used for bodyside liner 24. For example, bodyside liner 24 may be composed of a meltblown or spunbonded web of polyolefin fibers. Bodyside liner 24 may also be a bonded-carded-web composed of natural and/or synthetic fibers.

Bodyside liner 24 may be composed of a substantially hydrophobic and substantially nonwettable material, with the hydrophobic material optionally being treated with a surfactant or otherwise processed to impart a desired level of wettability and hydrophilicity.

In a preferred embodiment of the invention, bodyside liner 24 is extensible, preferably resiliently extensible, in at least one direction. "Resiliently extensible" can be defined as a material that retracts to substantially its original length or width upon release of an extending force. For example, a bodyside liner that is extensible 200% from its original length, that retracts to 150% of its original length may be considered resiliently extensible since a 75% return from the total amount of extension shows resilience.

Among other materials, bodyside liner 24 can be a nonwoven, spunbonded polypropylene fabric. See U.S. Pat. No. 5,226,992 to Morman et al, hereby incorporated by reference in its entirety, to the extent it is consistent with the disclosure herein, for teaching various materials which can be used in forming bodyside liner 24. The fabric can be creped or necked such that it is extensible in at least one of, or both of, the longitudinal direction "L" and the cross direction "C".

Bodyside liner 24 may comprise a multiplicity of components, layers, or partial layers, which correspond to any of the materials disclosed herein, as well as others known in the art. The fabric can be treated with a selected amount of surfactant, such as about 0.28% Trition X-102 surfactant available from Rohm and Haas Corp. of Philadelphia, Pa. The surfactant can be applied by any conventional means such as spraying, printing, brush coating or the like.

In yet another embodiment of the present invention, bodyside liner 24 can comprise a stretch-bonded laminate having appropriate elasticity and width to create overall surface contact between absorbent article 8 and the body of a user.

A stretch-bonded laminate comprises at least a two-layered composite in which one layer is a gatherable layer and the other layer a stretchable layer. The layers are joined together when the stretchable layer is in a stretched condition so that;, upon relaxing the composite of the joined layers, the gatherable layer is gathered. The stretchable layer can be a film of stretchable material, such as a layer of styrene ethylene butylene styrene copolymer or other elastomeric polymer, or a plurality of optionally spaced strands of a stretchable material such as latex. Other materials with similar properties may also be provided integral with or attached to bodyside liner 24. Such materials should not interfere with the soft texture of bodyside liner 24 against the skin of a user.

Bodyside liner 24 preferably has an extensibility of at least about 30%, more preferably at least about 200%, in the cross-direction "C". In some embodiments, bodyside liner 24 additionally can have similar extensibility in longitudinal direction "L". In other embodiments, bodyside liner 24 can be extensible only in longitudinal direction "L".

Outer cover 26 preferably comprises a first material extending over and about substantially the entirety of the overall area of the absorbent article 8, and capable of being extended in at least the cross-direction "C". Such materials include knitted and loosely woven fabrics, bonded carded webs, spunbonded webs and meltblown webs. A meltblown web typically includes meltblown microfibers. The material may also have multiple layers such as, for example, multiple spunbonded layers and/or meltblown layers. The material may be made of polymers such as, for example, polyolefins. Exemplary polyolefins include polypropylene, polyethylene, ethylene copolymers and propylene copolymers. See U.S. Pat. No. 5,226,992 to Morman et al., hereby incorporated by reference in its entirety to the extent it is consistent (not contradictory) herewith, for teaching various materials which can be used to form outer cover 26. A preferred material for the outer cover layer 26 can comprise an extensible film laminated to a necked nonwoven spun-bonded material.

Alternative constructions of outer cover 26 may include a woven or non-woven fibrous web layer which has been totally or partially constructed or treated to impart the desired levels of liquid impermeability to selected regions thereof, such as regions that are adjacent or proximate absorbent pad 38. Optionally, in some embodiments, an additional outer cover layer may overlie outer cover 26.

Outer cover 26 may optionally be composed of microporous, breathable material that enables vapors to escape from the absorbent article while preventing liquid exudates from passing through. For example, a suitable microporous film is a material known as PMP-1, which is available from Mitsui Toatsu Chemicals, Inc. a company having offices in Tokyo, Japan: or polyolefin film known as XKO-8044 and available from 3M Company of Minneapolis, Minn.

In another embodiment of the invention, outer cover 26 can be a nonwoven, spunbonded polypropylene fabric. The fabric can be creped or necked such that it is extensible in at least one of the "L" and "C" directions or in both the longitudinal direction "L" and the cross direction "C". Outer cover 26 can have an extensibility of at least about 30% and preferably at least about 200% in the cross-direction "C". In some embodiments, outer cover 26 additionally can have similar extensibility in longitudinal direction "L".

Other materials having other advantageous characteristics are also useful as outer cover 26. For example, outer cover 26 can comprise a stretch-bonded laminate. Methods of making such materials are known to those skilled in the art.

Preferably both bodyside liner 24 and outer cover 26 are extensible materials. Such extensibility should enable both layers to be extended in the same direction. At least one of bodyside liner 24 and outer cover 26 preferably is resiliently extensible, i.e. retractable to at least about 75% of the amount of extension upon release of the extending force. In such embodiments, at least one of bodyside liner 24 and outer cover 26 can return absorbent article 8 to substantially its original size and shape upon release of fastening tabs 20, 22 or other such restraints. In such an instance, the element that is merely extensible (e.g. no retractability forces) can follow the retractable liner/cover to the restorative size upon release. In other embodiments, both bodyside liner 24 and outer cover 26 can be resiliently extensible, and thus can and do assist each other in returning absorbent article 8 substantially to its earlier relaxed size and shape upon release of fastening tabs 20, 22.

Leg elastics 28 may be formed from separate materials which are attached to outer cover 26 and/or bodyside liner 24. Materials suitable for forming the leg elastics include LYCRA® strands, ribbons, or one or more layers of a polymeric and/or elastomeric material that may be adhered to absorbent article 8, thus forming leg elastics 28, while in a stretched or extended position. Leg elastics 28 provide limited extensibility of the absorbent article in longitudinal direction "L", from and to a relaxed condition. Alternatively, the material forming leg elastic 28 can be attached, in a relaxed condition, to absorbent article 8 while the article is pleated, such that elastic constrictive forces are imparted to at least crotch portion 18 of absorbent article 8 when the leg elastic is elongated along the length of the absorbent article.

In embodiments where outer cover 26 and/or bodyside liner 24 are formed from materials at least stretchable in longitudinal direction "L", extensible leg elastics 28 need not be provided for absorbent article 8.

Opposing left and right spaced containment flaps 30, 32 extend longitudinally along the length of absorbent article 8 inwardly of respective side edges 34, 36 of the absorbent article. In such embodiments as in FIGS. 1 and 2, containment flaps 30, 32 are typically secured to bodyside liner 24. Dashed lines 56 indicate where the entire surfaces of containment flaps 30, 32 facing bodyside liner 24 are secured to the bodyside liner outwardly from crotch portion 18. Inwardly from dashed lines 56, containment flaps 30, 32 are secured to bodyside liner 24 only at inward edges thereof, and thus can stand up or otherwise open to receive and restrain exudates.

Exemplary containment flaps are set forth in U.S. Pat. No. 4,704,116 issued Nov. 3, 1987 to K. Enloe, the disclosure of which is hereby incorporated by reference in its entirety to the extent that it is consistent (not contradictory) herewith.

Waist elastics (not shown) generally extend about the waist of absorbent article 8. Front waist elastics and rear waist elastics (not shown) generally comprise strands, ribbons or one or more layers of a polymeric and/or elastomeric material which can be adhered or otherwise mounted in absorbent article 8 while the elastic is in a stretched condition. Waist elastics can comprise one or more individual strands of elastomeric material, preferably in a spatially separated, generally parallel arrangement.

In some embodiments comprising extensible outer covers 26 and/or extensible bodyside liners 24, waist elastics can be omitted. Extensible bodyside liner 24 and extensible outer cover 26 can obviate the need for waist elastics while retaining the appropriate stretch function.

Absorbent pad 38 may be manufactured in a wide variety of sizes and shapes (for example, rectangular, trapezoidal, T-shape, I-shape, hourglass shape, etc.) and from a wide variety of materials. The size, and absorbent capacity, of absorbent pad 38 should be compatible with the size of the intended wearer and the anticipated liquid loading imparted by the intended use of the absorbent pad.

Absorbent pad 38 contains absorbent core 44 enveloped by first folded layer 40 and second folded barrier layer 42. Adhesive 46 preferably comprises cold adhesive applied to first folded layer 40 and/or second folded barrier 42 at least outwardly of the outer perimeter of absorbent core 44. Other known adhesives or bonding techniques may be utilized in place of cold adhesive to secure first surface 48 of first folded layer 40 to first surface 52 of second folded barrier layer 42.

First folded layer 40 typically comprises a single-ply, low porosity creped wadding tissue or the like. Other materials can also function as first folded layer 40 provided the proper porosity and other characteristics are present. First folded layer 40 generally comprises a substantially non-extensible material, such as a tissue.

Second folded barrier layer 42 typically comprises a tissue material. Thus, second folded barrier layer 42 provides a barrier to superabsorbent material migrating from absorbent core 44 toward bodyside liner 24. Second folded barrier layer 42 can comprise a non-extensible material.

Other materials having suitable characteristics may also be utilized for first and second folded layers 40, 42. First and second folded layers 40, 42 can also comprise multiple layers of various materials secured to each other.

As shown in FIG. 2, first and second folded layers 40, 42 can include T-folds 70, 72, 74, 76. Any number of folds from at least one, to a multiplicity of folds encompassing the entire surfaces of the layers, can be utilized for folded layers 40, 42. While FIG. 2 shows only two folds for each of the folded layers 40, 42, substantially the entire width of each of the respective folded layers can comprise folds. Thus no unfolded regions, such as the region between T-folds 70, 72 shown in FIG. 2, need be present. However, unfolded regions, where first and second folded layers 40, 42 are not folded, generally are present in many embodiments of the folded layers.

Many types of folds can be utilized for the invention. For example, FIG. 3 shows a cross-section view of another embodiment of the invention including C-folds 86, 88 for first folded layer 40 and C-folds 90, 92 for second folded barrier layer 42.

In other embodiments, the folds for either of first folded layer 40 or second folded layer 42 can comprise multiple pleats spaced across the width of absorbent article 8.

In most embodiments, folds in first folded layer 40 and second folded layer 42 open in cross-direction "C" as illustrated in FIGS. 2 and 3. However, in embodiments having an outer cover 24 and a bodyside liner 26 extensible in longitudinal direction "L", folds in respective first and second folded layers 40, 42 can open in the longitudinal direction.

Other types of folds can include corrugations. As shown in absorbent pad 38 of FIG. 4, first folded layer 40 and second folded barrier layer 42 each have a plurality of corrugations extending along substantially the entire length of absorbent article 8. Such corrugations enable expansion of the respective folded layers, in combination with bodyside liner 24 and outer cover 26, in cross-direction "C". Corrugations, where used, preferably extend over substantially the entire surface area of folded layers 40. 42.

Figure 4:
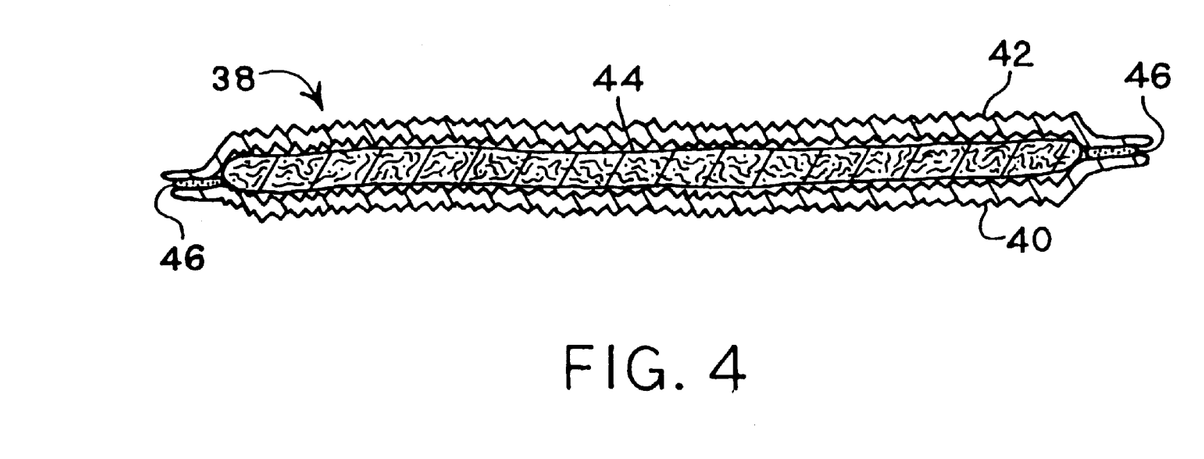
FIG. 4 shows a cross section of a third embodiment of an absorbent pad of the invention wherein the folds comprehend corrugations.

In FIG. 4, adhesive 46 secures corrugations of first folded layer 40 to corrugations of second folded barrier layer 42 outwardly about the perimeter of absorbent core 44. Thus, first folded layer 40, second folded barrier layer 42, and absorbent core 44, in combination form absorbent pad 38.

In other embodiments, corrugations can be formed in first folded layer 40 and second folded barrier layer 42 to enable expansion of absorbent article 8 in longitudinal direction "L".

Absorbent core 44 suitably comprises a matrix of hydrophilic fibers, such as a web of cellulosic fluff, preferably in combination with a high-absorbency material commonly known as superabsorbent material. In a preferred embodiment, absorbent core 44 comprises a mixture of superabsorbent hydrogel-forming material and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent core 44 may comprise a laminate of fibrous webs and superabsorbent material or other suitable means of maintaining a superabsorbent material in a localized area.

The high-absorbency material in absorbent core 44 can be selected from natural, synthetic and modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Figure 5:
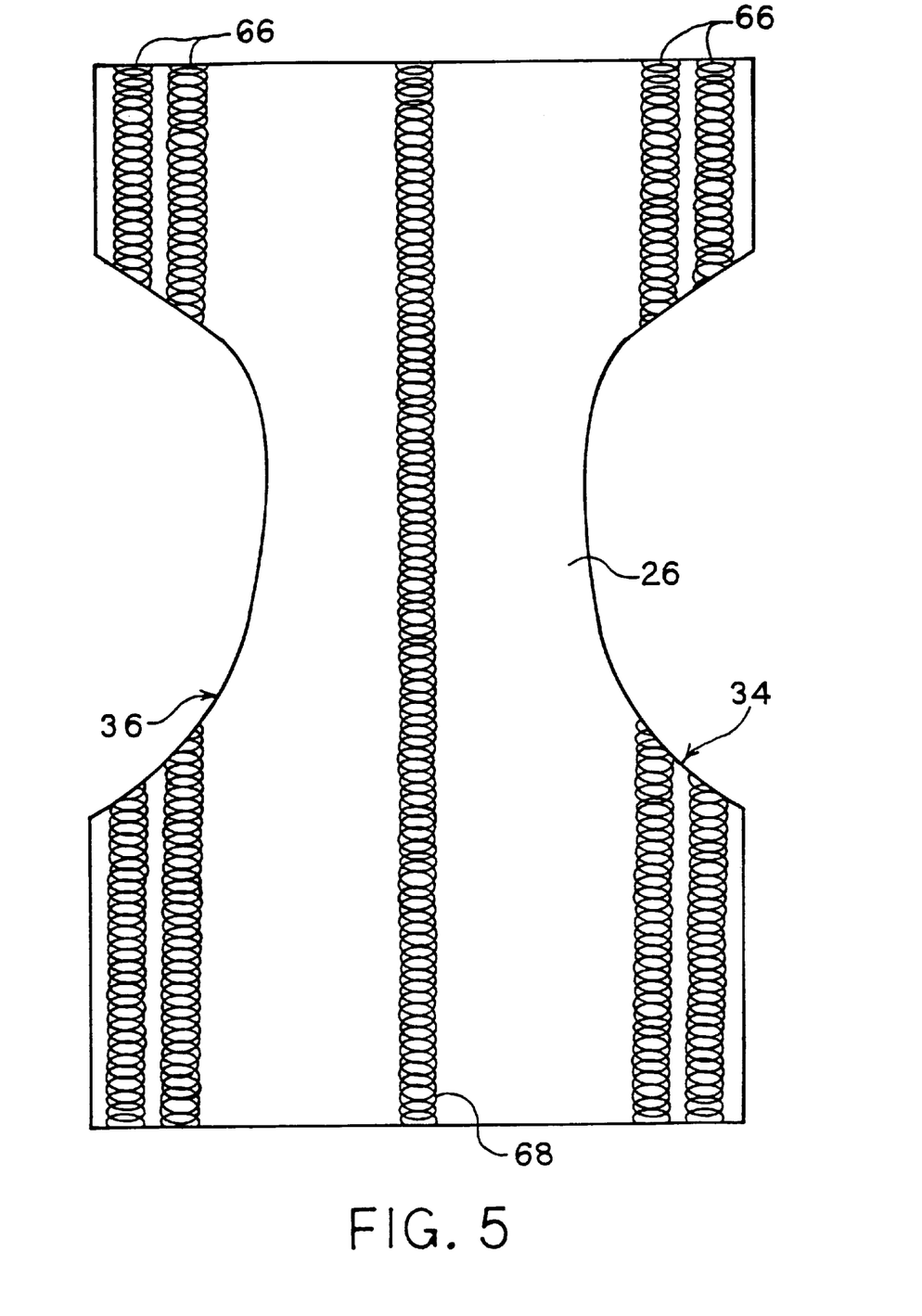
FIG. 5 shows a top view of an inner surface of an outer cover having adhesive applied thereto.

Bodyside liner 24 is secured to outer cover 26 about at least an outer perimeter of absorbent pad 38. Typically, such securement is provided by adhesive 66. As shown in FIG. 5, adhesive 66 can comprise laterally spaced arrays of swirl patterns of adhesive applied along longitudinal direction "L" to opposing sides of second surface 64 of outer cover 26 outwardly from the intended location of absorbent pad 38. Adhesive 66 can also comprise overlapping swirl patterns of adhesive. As described earlier, adhesive 66 secures bodyside liner 24 and outer cover 26 along side edges 34. 36. Pattern of adhesive 66 can also secure at least part of second surface 50 of folded layer 40 to outer cover 26 at longitudinal sections thereof as indicated by the cross-section view of FIG. 2. Line of adhesive 68 can also comprise a swirl pattern as illustrated in FIG. 5.

In embodiments including no added leg elastics adhesively secured to outer cover 26, adhesive (not shown) can be applied to the outer cover adjacent leg openings in crotch portion 18. Such adhesive can provide sufficient sealing to retain absorbent pad 38 in absorbent article 8 and can prevent superabsorbent material or other material from escaping the article. Likewise, even in embodiments having leg elastics, adhesive (not shown) can be applied at side edges 34, 36 of absorbent article 8 to retain absorbent materials between bodyside liner 24 and outer cover 26.

As shown in FIG. 3, adhesive 66 can be disposed on second surface 60 of bodyside liner 24 instead of on outer cover 26 when forming absorbent article 8. In such an arrangement, manufacturing steps for absorbent article 8 are desirably reversed.

In instances where bodyside liner 24 and outer cover 26 are extensible in both cross direction "C" and longitudinal direction "L", adhesive 66 can comprise other patterns not including solid lines of adhesive in the longitudinal direction. For example, adhesive 66 could comprise an angled pattern of adhesives or spaced unconnected areas of adhesive applied by intermittent operation of adhesive applicators or by printing rolls. Such patterns prevent or limit adhesive 66 from "locking up" stretch of outer cover 26 in longitudinal direction "L" or cross direction "C". As used herein, "locking up" means an adhesive or glue preventing an extensible material from extending the amount designed because of the adhesive creating a bond at at least a surface of the extensible material.

FIG. 3 shows line of adhesive 68 and additional lines of adhesive 94, 96 spaced outwardly therefrom on second inner surface 64 of outer cover 26 and extending in longitudinal direction "L". Line of adhesive 68 and additional lines 94, 96 improve end sealing of individual ends of bodyside liner 24 and outer cover 26 at front and rear edges 12, 16 of absorbent articles 8 when the articles are separated from each other in the manufacturing process. Thus, while lines of adhesive 68, 94, 96 are optional, at least some lines of adhesive are preferred.

Lines of adhesive 94, 96 cannot pass through the material of folded layer 40. If adhesive migrates through folded layer 40 and secures the layer surface-to-surface at either of C-folds 86, 88, the C-folds will not open and extend to protect the folded layer from tearing. Therefore, in embodiments having lines of adhesive 94, 96, as shown in FIG. 3, minimal adhesive must be utilized to avoid having the adhesive blot through folded layer 40.

The arrangement shown in FIG. 3 can be reversed by placing lines of adhesive 94, 96 adjacent bodyside liner 24, and preferably spaced outwardly from surge layer 78. Further, although three lines of adhesive 68, 94, 96 are shown in FIG. 3, any number of lines of adhesive can be utilized, so long as the lines of adhesive do not significantly prevent folds from opening and extending from folded layers 40, 42.

Other patterns of adhesive, such as intermittent lines of adhesive, can be utilized instead of solid lines of adhesive 68, 94, 96.

Surge layer 78 generally is located between second folded layer 42 and bodyside liner 24. Surge layer 78 assists in spread of exudates over a substantial portion of absorbent pad 38. Thus surge layer 78 assists absorbent pad 38 in absorbing a sudden large amount of urine or other body exudates. First surface 80 of surge layer 78 is in surface-to-surface contact with second surface 54 of second folded barrier layer 42 and second surface 82 of the surge layer is in surface-to-surface contact with second surface 60 of bodyside liner 24.

Surge layer 78 can comprise materials set forth in U.S. Pat. No. 5,486,166 issued Jan. 23, 1996 to C. Ellis and D. Bishop, entitled, "Fibrous Nonwoven Web Surge Layer for Personal Care Absorbent Articles and the Like"; and U.S. Pat. No. 5,490,846 issued Feb. 13, 1996 to C. Ellis and R. Everett, entitled, "Improved Surge Management Fibrous Nonwoven Web for Personal Care Absorbent Articles and the Like"; the disclosures of which are herein incorporated by reference to the extent the disclosures are consistent (not contradictory) with the information disclosed herein. Further, other surge layer materials known in the art can also be utilized.

Optionally, a line of adhesive (not shown) extending in the longitudinal direction "L" in a manner similar to line of adhesive 84 can be located between surge layer 78 and absorbent pad 38. Such a line of adhesive prevents absorbent pad 38 from shifting laterally a significant distance, while enabling bodyside liner 24 to extend, at least in the cross-direction "C". Such an arrangement ensures absorbent pad 38 remains centered in absorbent article 8.

In another embodiment of the invention, line of adhesive 84, and any adhesive disposed between surge layer 78 and absorbent pad 38, can be located at spaced intervals along longitudinal direction "L". For example, line of adhesive 84 can comprise a broken line of adhesive sections intermittently sprayed onto surge layer 78 or bodyside liner 24. Thus, for embodiments having bodyside liner 24 and outer cover 26 both extensible in cross-direction "C" and longitudinal direction "L", adhesive 84 will not significantly lock up, or prevent extension of the bodyside liner in the longitudinal direction. Any adhesive between surge layer 78 and absorbent pad 38 can be applied in a similar manner.

Adhesive 84 can comprise hot melt adhesive applied to second surface 60 of bodyside liner 24, and second surface 82 of surge layer 78. Thus, second surface 82 of surge layer 78 is secured by the hot melt adhesive in surface-to-surface relationship with second surface 60 of bodyside liner 24.

In preferred operation, bodyside liner 24, outer cover 26, and first and second folded layers 40, 42 are generally all extendible in the same direction. During placement of absorbent article 8 on a wearer, bodyside liner 24 and outer cover 26 extend, and extension of folded layers 40, 42 at folds thereof prevent tearing of either of the first and second folded layers, thus avoiding release of superabsorbent material from absorbent pad 38. In some absorbent articles, all of the elements can be extendible in cross-direction "C". In other articles, all of the elements can be extendible in longitudinal direction "L".

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An absorbent pad for use in an absorbent article, said absorbent pad having a cross-direction extending across a width of said absorbent pad and a longitudinal direction extending along a length of said absorbent pad, said absorbent pad comprising:
   (a) an absorbent core having an outer perimeter, a first side, and a second side opposing said first side;
   (b) a first folded layer of non-extensible material, wherein said first folded layer includes at least one fold therein and said first folded layer is disposed adjacent said first side of said absorbent core;
   (c) a second folded layer of non-extensible material acting as a barrier layer, wherein said second folded layer has at least one fold and said second folded layer is disposed adjacent said second side of said absorbent core, and wherein said first folded layer and said second folded layer extend in said cross-direction beyond said outer perimeter of said absorbent core; and
   (d) an adhesive securing first and second ends of said first folded layer to first and second ends of said second folded layer, respectively, wherein said first and second ends of said first and second folded layers are located outwardly of said outer perimeter of said absorbent core so that said first folded layer and said second folded layer enclose said absorbent core between said first and second ends thereof.

2. An absorbent pad as in claim 1 wherein said at least one fold of said first folded layer includes a first pleat, and a second pleat which is across the width of said absorbent pad from said first pleat.

3. An absorbent pad as in claim 1 wherein said at least one fold of said first folded layer includes a multiplicity of corrugations, said multiplicity of corrugations providing for extension of said first folded layer in the cross-direction.

4. An absorbent pad as in claim 3 wherein substantially an entirety of said first and second surfaces of said first folded layer is encompassed by a pattern of said multiplicity of corrugations.

5. An absorbent pad as in claim 1 wherein said at least one fold of said first folded layer includes at least one T-fold.

6. An absorbent pad as in claim 1 wherein said at least one fold of said first folded layer includes at least one C-fold.

7. An absorbent pad as in claim 1 wherein said first folded layer and said second folded layer both are made of non-extensible tissue material.

8. An absorbent article including a rear portion having a rear edge, a front portion having a front edge, and a crotch portion connecting said rear portion and said front portion, said absorbent article having a cross-direction extending across a width of said absorbent article and a longitudinal direction extending along a length of said absorbent article through said front, crotch, and rear portions, said absorbent article comprising:
   (a) an absorbent pad including an absorbent core and at least one folded layer of material, wherein said absorbent core has an outer perimeter, a first side, a second side, and absorbent material located therewithin, and wherein said at least one folded layer is made of substantially non-extensible material, said at least one folded layer including at least one fold therein, said at least one folded layer having a first surface, and a second surface which opposes the first surface, the first surface of said at least one folded layer being unadheringly disposed immediately adjacent the first side of said absorbent core;
   (b) an outer cover made of an extensible material, wherein said outer cover has a first surface and a second surface, the second surface of said outer cover opposing the first surface of said outer cover, the second surface of said at least one folded layer being disposed in surface-to-surface relationship with the first surface of said outer cover; and
   (c) a pattern of adhesive disposed at least in part between said at least one folded layer and said outer cover, wherein said pattern of adhesive mounts said at least one folded layer to said outer cover such that, in response to said extensible material of said outer cover being extended in the cross-direction of said absorbent article, said at least one folded layer can extend in the cross-direction of said absorbent article by opening of the at least one fold so that said at least one folded layer does not tear and thereby release said absorbent material from said absorbent core of said absorbent pad.

9. An absorbent article as in claim 8 wherein said at least one fold includes a first pleat, and a second pleat, said second pleat being spaced widthwise of said absorbent article from said first pleat.

10. An absorbent article as in claim 8 wherein said non-extensible material of said at least one folded layer is a tissue material.

11. An absorbent article as in claim 8 wherein said at least one fold of said at least one folded layer is a corrugation, said at least one folded layer having a multiplicity of corrugations, and said multiplicity of corrugations allowing for extension of said at least one folded layer in the cross-direction.

12. An absorbent article as in claim 11 wherein substantially an entirety of the first surface and the second surface of said at least one folded layer is encompassed by a pattern of the multiplicity of corrugations.

13. An absorbent article as in claim 8 wherein the at least one fold of said at least one folded layer comprises at least one T-fold.

14. An absorbent article as in claim 8 wherein the at least one fold of said at least one folded layer comprises at least one C-fold.

15. An absorbent article as in claim 8 wherein said pattern of adhesive includes at least one line of adhesive material extending along said length of said absorbent article, said at least one fine of adhesive being disposed between said outer cover and said at least one folded layer, and said at least one line of adhesive securing said outer cover to said at least one folded layer at an unfolded portion of said at least one folded layer.

16. An absorbent article as in claim 15, further comprising at least a second line of adhesive extending along the length of said absorbent article, said at least second line of adhesive being disposed between said outer cover and said at least one folded layer, and said at least second line of adhesive securing said outer cover to said at least one folded layer at a second unfolded portion of said at least one folded layer.

17. An absorbent article as in claim 16, further comprising a bodyside liner, wherein said at least one line of adhesive and said at least second line of adhesive both extend effectively along an entirety of the length of said absorbent article and thereby assist in sealing ends of said bodyside liner and said outer cover at said front and rear edges of said absorbent article.

18. An absorbent article as in claim 8, further comprising a bodyside liner, having a first surface which is capable of contacting the body of a wearer of said absorbent article, and a second surface opposed to the first surface of said bodyside liner, wherein the second surface of said bodyside liner is mounted in surface-to-surface relationship on at least a portion of the first surface of said outer cover.

19. An absorbent article as in claim 18 wherein said at least one folded layer comprises a first folded layer of material and a second folded layer of material, said second folded layer of material acting as a barrier layer and being disposed between the second side of said absorbent core and the second surface of said bodyside liner, said second folded layer having at least one fold therein.

20. An absorbent article as in claim 19 wherein said second folded layer is adhesively secured to said first folded layer outwardly of the outer perimeter of said absorbent core.

21. An absorbent article as in claim 19, wherein said first folded layer and said second folded layer both are made of non-extensible tissue material.

22. An absorbent article as in claim 18 wherein said bodyside liner is extensible in at least the cross-direction.

23. An absorbent article as in claim 19 wherein said bodyside liner, said outer cover, said first folded layer, and said second folded layer all are extendible in the cross-direction during placement of said absorbent article on the wearer of said absorbent article, said second folded layer being extensible at said at least one fold so as to prevent tearing off said second folded layer during extension of said absorbent article, and thus avoiding release of said superabsorbent material from said absorbent core.

24. An absorbent article including a rear portion having a rear edge, a front portion having a front edge, and a crotch portion connecting said rear portion and said front portion, said absorbent article having a cross-direction extending across a width of said absorbent article and a longitudinal direction extending along a length of said absorbent article through said front portion, said crotch portion, and said rear portion, said absorbent article comprising:
(a) an outer cover made of an extensible material, wherein said outer cover has a first surface, which is an inner surface, and a second surface which opposes the first surface and which is an outer surface;
(b) a bodyside liner made of an extensible material, wherein said bodyside liner has a first surface which is capable of contacting the body of a wearer of said absorbent article, and a second surface which opposes the first surface of said bodyside liner, and wherein the second surface of said bodyside liner is in surface-to-surface relationship with at least a portion of the first surface of said outer cover;
(c) an absorbent pad disposed between said bodyside liner and said outer cover, wherein said absorbent pad includes an absorbent core having an outer perimeter, a first side, a second side opposing said first side, a first folded layer of material disposed between said first side of said absorbent core and the first surface of said outer cover, and a second folded layer of material, which is a barrier layer and which is disposed between said second side of said absorbent core and the second surface of said bodyside liner; and
(d) a pattern of adhesive disposed between one of a group consisting of (i) the second surface of said outer cover and the second surface of said first folded layer and (ii) the second surface of said bodyside liner and the second surface of said second folded layer, wherein the pattern of adhesive accommodates extending one of said first folded layer and said second folded layer when said extensible material of one of said outer cover and said bodyside liner is extended.

25. An absorbent article as in claim 24 wherein said pattern of adhesive is disposed between the second surface of said outer cover and the second surface of said first folded layer such that extending said extendible material of said outer cover and said bodyside liner can extend said first folded layer and said second folded layer at respective folds in the respective first and second folded layers and within said absorbent article.

26. An absorbent article as in claim 25 wherein said pattern of adhesive includes an array of adhesive extending in the longitudinal direction on opposing sides of the second surface of said outer cover, outwardly from the second surface of said first folded layer of said absorbent pad.

27. An absorbent article as in claim 24 wherein said pattern of adhesive is disposed between the second surface of said bodyside liner and the second surface of said second folded layer such that extending said extendible material of one of said outer cover and said bodyside liner can extend said first folded layer and said second folded layer, respectively, at respective folds in the respective first and second folded layers.

28. An absorbent article as in claim 27 wherein said pattern of adhesive extends in said longitudinal direction on opposing sides of the second surface of said bodyside liner, outwardly from the second surface of said second folded layer of said absorbent pad.

29. An absorbent article as in claim 24 wherein said first folded layer includes at least one fold having first and second pleats.

30. An absorbent article as in claim 29 wherein said pattern of adhesive includes at least a first line of adhesive extending in the longitudinal direction and being disposed between the second surface of said outer cover and the second surface of said first folded layer.

31. An absorbent article as in claim 30 wherein said at least first line of adhesive assists in maintaining alignment of said absorbent pad in said absorbent article.

32. An absorbent article as in claim 29, further comprising a second fold having first and second pleats on said first folded layer, wherein said at least first line of adhesive is disposed between the at least one fold and the second fold such that extending said extendible material of said outer cover in said cross-direction causes said first folded layer to extend at the first pleat of the at least one fold and at the second pleat of the second fold.

33. An absorbent article as in claim 24 wherein extensible material of said bodyside liner is resiliently extensible.

34. An absorbent article as in claim 33 wherein said extensible materials of said bodyside liner and said outer cover are extensible in at least the cross-direction, said first folded layer and said second folded layer each having at least one fold extending along substantially an entirety of the length of said absorbent article in the longitudinal direction.

35. An absorbent article as in claim 34 wherein said bodyside liner, said outer cover, said first folded layer, and said second folded layer all increase cross-direction dimension during placement of said absorbent article on the wearer, such increase in cross-direction dimension of said first folded layer and said second folded layer being enabled by the ability of said at least one fold in said first folded layer and said at least one fold in said second folded layer to unfold.

36. An absorbent article as in claim 34 wherein said pattern of adhesive includes laterally spaced arrays of swirls of adhesive disposed along a length of the second surface of said outer cover, outwardly from the second surface of said first folded layer.

* * * * *

UNITED STATES PATENT AND TRADEMARK OFFICE
CERTIFICATE OF CORRECTION

PATENT NO.    : 6,149,638
DATED         : November 21, 2000
INVENTOR(S)   : Robert Eugene Vogt et al.

It is certified that error appears in the above-identified patent and that said Letters Patent is hereby corrected as shown below:

Column 5
Line 56, between "C" and "T-folds", delete "." and insert -- , -- in place thereof.
Line 38, delete ";".

Column 14, claim 15,
Line 63, delete "fine" and insert -- line -- in place thereof.

Drawings,
Figure 3, Sheet 3 of 4, lead line of 44 should extend down to absorbent core.

Signed and Sealed this

Twenty-sixth Day of March, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO. : 6,149,638
DATED : November 21, 2000
INVENTOR(S) : Robert Eugene Vogt and Timothy James Blenke It is certified that error appears in the above-identified patent and that said Letters Patent is hereby corrected as shown below:

Title page,
Item [56], References Cited, U.S. PATENT DOCUMENTS, delete "10/1984" and substitute -- 5/1988 --.

Column 7,
Line 32, delete the return after "user." to form a single paragraph with the paragraph that starts with "A stretch-bonded".
Line 37, delete ";".

Column 18,
Line 4, delete "34" and substitute -- 24 --.

Signed and Sealed this

Twentieth Day of August, 2002

Attest:

Attesting Officer

JAMES E. ROGAN
Director of the United States Patent and Trademark Office